United States Patent [19]

Kaganov

[11] Patent Number: 5,096,565

[45] Date of Patent: Mar. 17, 1992

[54] SAFE FAILURE ION SELECTIVE COMBINATION ELECTRODE

[75] Inventor: Mark D. Kaganov, Lakewood, Colo.

[73] Assignee: Cobe Laboratories, Inc., Lakewood, Colo.

[21] Appl. No.: 597,048

[22] Filed: Oct. 15, 1990

Related U.S. Application Data

[63] Continuation of Ser. No. 377,887, Jul. 10, 1989.

[51] Int. Cl.[5] .......................................... G01N 27/333
[52] U.S. Cl. ............................... 204/401; 204/153.21;
204/416; 204/420; 204/433; 324/438
[58] Field of Search .................. 204/401, 433, 153.21,
204/416–420; 324/438

[56] References Cited

U.S. PATENT DOCUMENTS 3,681,025  8/1972  Dalgaard ..................... 324/438 X
4,189,367  2/1980  Connery et al. ................ 204/401
4,777,444  10/1988  Beijk et al. ...................... 324/439
4,829,253  5/1989  Koluvek ........................... 324/438

FOREIGN PATENT DOCUMENTS 3710992  10/1988  Fed. Rep. of Germany ...... 324/433
1129145  10/1968  United Kingdom ............. 324/438

OTHER PUBLICATIONS

Clifford A. Hampel, "The Encyclopedia of Electrochemistry", pp. 901–902, (1964).
J. Dobrzycki, Pomiary Automatyka Kontrola, vol. 21, No. 12, pp. 487–488, Dec. 1975.

Primary Examiner—T. Tung

[57] ABSTRACT

A safe failure ion selective combination electrode in which a signal unit provides a signal if combination electrode output falls outside a predetermined range.

3 Claims, 1 Drawing Sheet

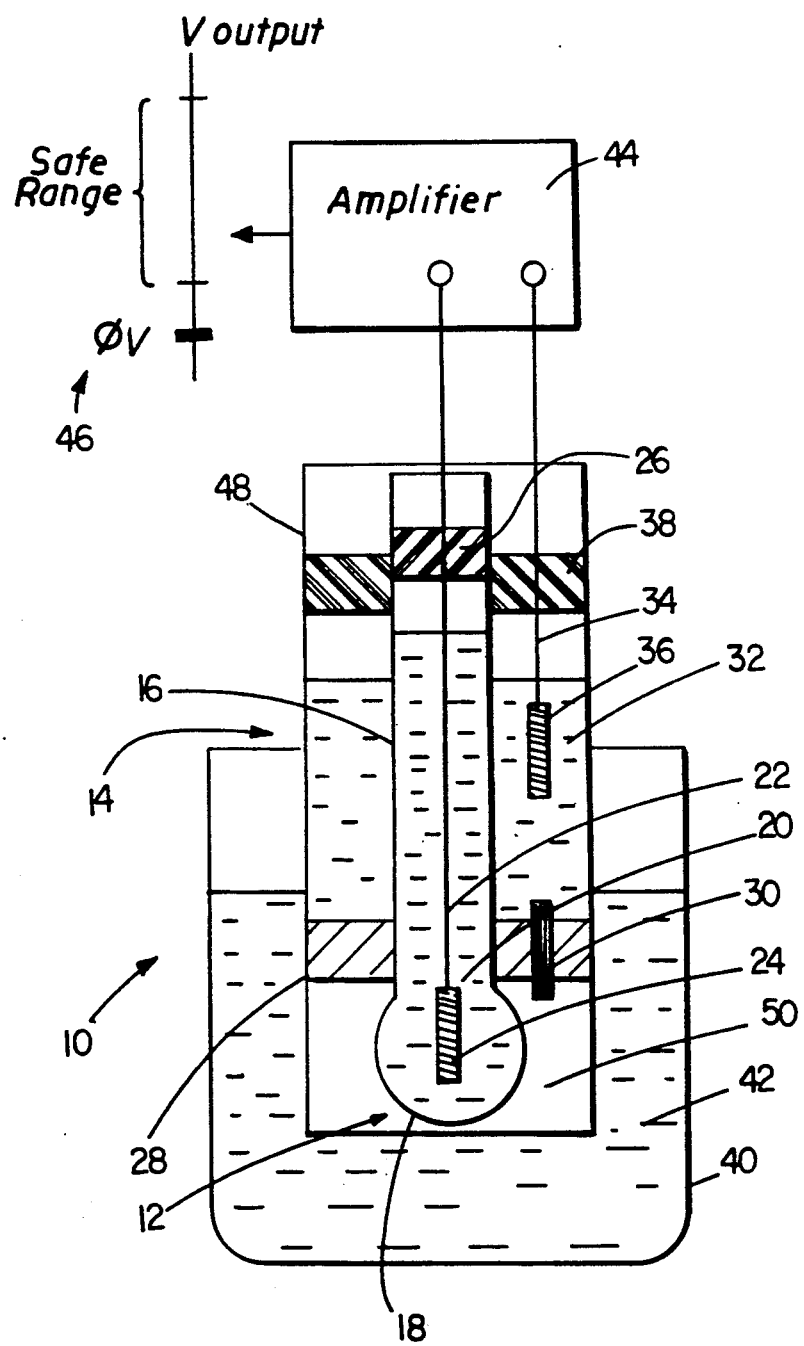
FIGURE

SAFE FAILURE ION SELECTIVE COMBINATION ELECTRODE

This is a continuation of co-pending application Ser. No. 07/377,887 filed on July 10, 1989.

FIELD OF THE INVENTION

This invention relates to ion selective combination electrodes, and more particularly to such devices which can detect and signal their own breakdown.

BACKGROUND OF THE INVENTION

General purpose pH combination electrodes that operate over the full pH range and provide an output of about minus 60 millivolts (mV) per unit of pH, output at pH 7.0 being zero mV are known. It is known also to shift the zero mV point, as to pH 4.0 or 10.0, to avoid automatic temperature compensating metering circuits, by varying internal solution formulation.

SUMMARY OF THE INVENTION

It has been discovered that an ion selective combination electrode in which zero mV output corresponds to ion concentrations, such as pH, outside a desired range makes it possible to detect an electrode's internal breakdown.

PREFERRED EMBODIMENT

The preferred embodiment is shown in the attached drawing, the structure and operation of which is then described.

DRAWING

In the drawing is shown a diagrammatic view of said preferred embodiment.

STRUCTURE

The preferred embodiment is indicated generally at 10 in the drawing.

The ion selective combination electrode 10 has as two functional parts an ion selective electrode indicated generally at 12 and a reference electrode indicated generally at 14.

Ion selective electrode 12 has a glass stem 16 in communication with ion selective glass bulb 18. Within the vessel defined by stem 16 and bulb 18 is solution 20, in which hang silver wire 22 with dependent therefrom silver chloride billet 24. Inner solution 20 is a pH 5.0 solution prepared by adding Potassium Acide Phthalate (Merck, AR Primary Standard), 0.05 mols phthalate, to 1.8 mols of potassium chloride, the whole made up to a one liter quantity with deionized water, and adjusted to its final pH with NaOH. Seal 26 provides a seal around tubular portion 16 and wire 22.

Bushing 28, which has liquid junction 30 extending therethrough, is an annulus which positions electrode 12 within electrode 14. The latter contains, above bushing 28, a standard prior art reference electrolyte solution 32. Silver wire 34 extends into solution 32, and has dependent from it silver chloride billet 36. Seal 38, which is annular, seals wire 34 and both electrodes therearound.

Container 40 is shown with, within it, a solution 42 the pH of which is being monitored.

Wires 22 and 34 are connected with amplifier 44, which provides a voltage output reflecting the input form the two wires. The unit indicated diagrammatically and generally at 46 has control and alarm circuits and provides a warning signal if voltage goes to zero; the unit 46 is programmed so that predetermined desired voltages are in the pH range of 6.5 to 8.2, while zero voltage is at pH 5.5.

Outer wall 48 provides both the wall for reference electrode 14 and a zone 50 whereat solution being tested can be in contact with bulb 18 and junction 30, for sealed electrical contact therethrough (through holes not shown).

The following chart compares the preferred embodiment

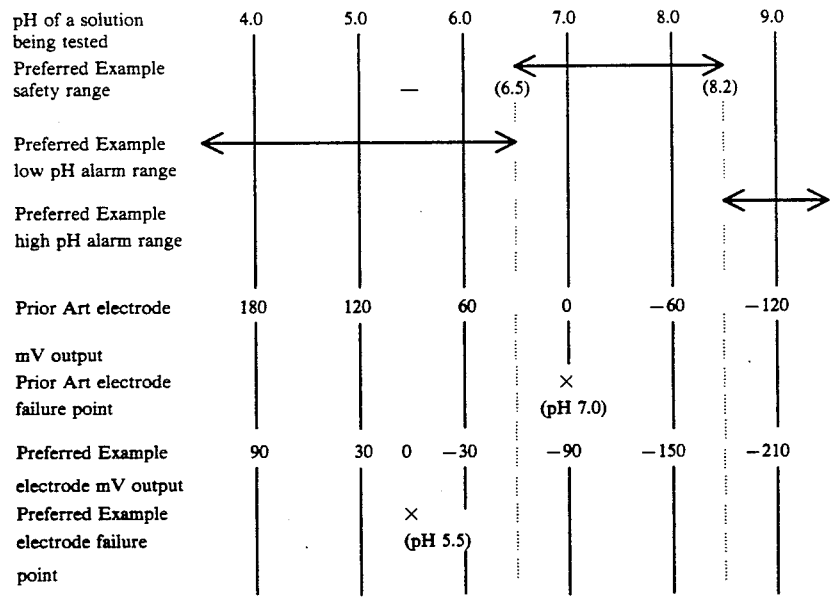

OPERATION

In normal use, with the combination electrode 10 in the test liquid 42, pH is within the safe range set into unit 46, and is therein monitored. If tube 16 ruptures, voltage goes to zero, which in the invention is outside the safe or predetermined operating range, and a signal circuit in unit 46 gives its signal. The signal is also given at other voltages outside the predeterminedly desired range.

Other embodiments within the following claims will appear to those skilled in the art.

What is claiemd is:

1. An ion selective combination electrode system for monitoring ion concentration of a test solution for which there is an associated predetermined safe ion concentration range comprising
    an ion selective electrode, said electrode including
        a vessel,
        an inner solution in said vessel,
        a first element in said inner solution, and
        a first electrical line for making an external electrical connection to said first element,
    a reference electrode including a second element and a second electrical line for making an external electrical connection to said second element,
        said ion selective electrode and said reference electrode being in an electrode subsystem providing an electrical output that varies as a function of ion concentration of said test solution,
        said electrical output having a predetermined safe electrical output range associated with said predetermined safe ion concentration range,
        said electrical output being outside said predetermined safe electrical output range when said electrode subsystem is malfunctioning, and
    a control unit electrically connected to said first and second lines to receive said electrical output,
        said unit being constructed to provide a warning signal if said electrical output is outside said predetermined safe electrical output range,
    wherein said electrode subsystem has a predetermined safe electrical output range that is a voltage range that does not include zero volt, and said electrical output is zero volt when said electrode subsystem malfunctions, and
    wherein said inner solution is selected to provide said voltage range that does not include zero volt.

2. An ion selective combination electrode system for monitoring ion concentration of a test solution for which there is an associated predetermined safe ion concentration range comprising
    an ion selective electrode, said electrode including
        a vessel,
        an inner solution in said vessel,
        a first element in said inner solution, and
        a first electrical line for making an external electrical connection to said first element.
    a reference electrode including a second element and a second electrical line for making an external electrical connection to said second element,
        said ion selective electrode and said reference electrode being in an electrode subsystem providing an electrical output that varies as a function of ion concentration of said test solution,
        said electrical output having a predetermined safe electrical output range associated with said predetermined safe ion concentration range,
        said electrical output being outside said predetermined safe electrical output range when said electrode subsystem is malfunctioning, and
    a control unit electrically connected to said first and second lines to receive said electrical output,
        said unit being constructed to provide a warning signal if said electrical output is outside said predetermined safe electrical output range,
    wherein said system monitors pH, and
    wherein said predetermined safe ion concentration range includes a pH value of 7.0, and said inner solution has a pH that is outside of said predetermined safe ion concentration range.

3. An ion selective combination electrode system for monitoring ion concentration of a test solution for which there is an associated predetermined safe pH range that includes a pH of 7 comprising
    an ion selective electrode, said electrode including
        a vessel,
        an inner solution in said vessel that has a pH outside of said predetermined safe pH range,
        a first element in said inner solution, and
        a first electrical line for making an external electrical connection to said first element,
    a reference electrode including a second element and a second electrical line for making an external electrical connection to said second element,
        said ion selective electrode and said reference electrode being in an electrode subsystem providing an output voltage that varies as a function of pH of said test solution,
        said output voltage having a predetermined safe output voltage range associated with said predetermined safe pH range, said predetermined safe output voltage range not including zero volt,
        said output voltage being zero when said vessel ruptures, and
    a control unit electrically connected to said first and second lines to receive said output voltage,
        said unit being constructed to provide a warning signal if said output voltage is outside said predetermined safe output voltage range.

* * * * *